United States Patent [19]

Raspanti

[11] Patent Number: 5,332,568
[45] Date of Patent: Jul. 26, 1994

[54] S-TRIAZINE DERIVATIVES HAVING LIGHT-PROTECTING ACTION

[75] Inventor: Giuseppe Raspanti, Bergamo, Italy

[73] Assignee: 3V Inc., Weehawken, N.J.

[21] Appl. No.: 63,748

[22] Filed: May 20, 1993

[51] Int. Cl.⁵ .................... A61K 7/42; C07D 405/12
[52] U.S. Cl. .................................. 424/59; 514/245; 514/198
[58] Field of Search .............. 544/198; 514/245; 424/59

[56] References Cited

U.S. PATENT DOCUMENTS 5,062,882  11/1991  Newton et al. ................ 544/198

Primary Examiner—John M. Ford
Assistant Examiner—Y. N. Gupta
Attorney, Agent, or Firm—Griffin, Butler, Whisenhunt & Kurtossy

[57] ABSTRACT

S-triazine derivatives of formula (I):

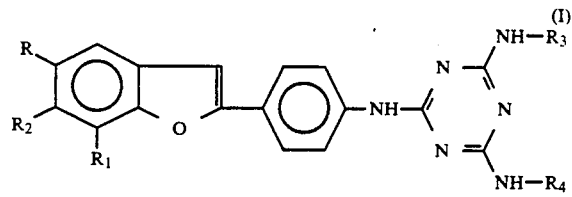

a process for the preparation thereof and the use thereof as light stabilisers.

8 Claims, No Drawings

S-TRIAZINE DERIVATIVES HAVING LIGHT-PROTECTING ACTION

The present invention relates to s-triazine derivatives, the process for the preparation thereof and the use thereof as light stabilisers.

The compounds of the invention have the following general formula (I)

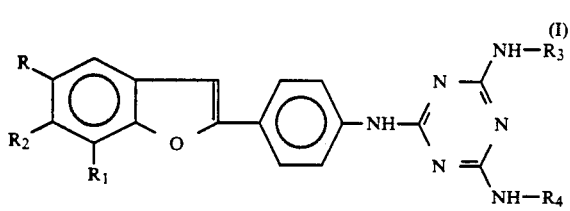

in which
R and $R_1$, which are the same or different, are hydrogen or $C_1-C_8$ straight or branched alkyl;
$R_2$ is hydrogen or $C_1-C_8$ straight or branched alkoxy;
$R_3$ and $R_4$, which are the same or different, are $C_1-C_{18}$ straight or branched alkyl, $C_5-C_{12}$ cycloalkyl optionally substituted with groups $C_1-C_8$ alkyl, optionally substituted aryl groups or a group of formula (II) or (III)

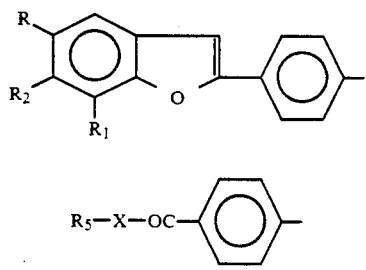

in which R, $R_1$ and $R_2$ have the meanings defined above, $R_5$ has the same meaning as $R_3$ and X is oxygen or the —NH— group or when X is oxygen $R_5$ can represent a group of formula (IV)

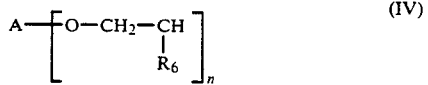

in which A is $C_1-C_8$ straight or branched alkyl, $C_5-C_8$ cycloalkyl, optionally substituted aryl, $R_6$ is hydrogen or methyl and n can be an integer from 1 to 10.

Examples of $C_1-C_8$ alkyl comprise methyl, ethyl, n-propyl, isopropyl, n-butyl, n-octyl.

Examples of $C_1-C_8$ alkoxy comprise methoxy, ethoxy, propoxy.

Examples of $C_5-C_{12}$ cycloalkyl optionally substituted with $C_1-C_8$ alkyl groups comprise cyclopentyl, cyclohexyl, 4-methylcyclohexyl.

Optionally substituted aryl is preferably phenyl or phenyl substituted with one to three substituents, which can be the same or different, selected from alkyl, $C_1-C_8$ alkoxy groups or halogen atoms.

Ultraviolet radiations of sunlight are known to exert a damaging action on skin tissue. In fact, the prolonged exposure to sunlight is considered to be the main cause in the development of degenerative processes and of some skin tumours.

Ultraviolet radiation is also known to cause degradation of synthetic polymers.

By using particular compounds, the so-called sunscreens, which are capable of absorbing the UV part of solar radiation, the damaging effects and the aging of the skin and polymer materials can be prevented or, at least, slowed down.

A number of substances have been studied and tested as protecting agents, and an extensive patent literature exists on this subject, in which compounds belonging to different chemical classes are proposed, which are capable of absorbing in the ultraviolet region, particularly the radiation from 290 to 360 nm.

The radiation from 290 to 320 nm (named UV-B) causes erythema to form, whereas the one from 320 to 400 nm (named UV-A) is responsible for skin suntan.

Sunscreens adsorbing in the UV-B region are widely used as protecting agents against sunburns; whereas the use of sunscreens to shield skin from UV-A radiations was unknown until some time ago, except for some cases of particular therapies.

However, recent researches evidenced that the continued and intensive UV-A radiation can also cause remarkable skin damages, particularly to persons having a very sensitive, delicate skin.

Only a few of the compounds proposed up to now as sunscreens proved suitable for the practical application. Among these, p-methoxy-cinnamic acid and p-dimethylaminobenzoic acid esters, benzotriazoles, hydroxybenzophenones and dibenzoylmethane derivatives.

The common drawback of all these compounds is the low power thereof to absorb the radiation from 290 to 360 nm. Therefore, it is necessary to use relatively large amounts thereof in cosmetic compositions to obtain an optimum light-protecting capability, accordingly the use thereof in practice can give rise to problems from the toxicologic and economic point of view.

In DE 3 205 398 Patent, s-triazine derivatives are disclosed, obtained by reacting trichlorotriazine with p-aminobenzoic acid esters, which derivatives have an absorption power much higher than those of the above cited chemical classes. However, these compounds only absorb in a restricted UV-B region and they are not suitable to exert a complete protecting action.

An optimum UV absorber should have the following characteristics:
1) high specific extinction to allow a low dosage and accordingly cost-savings and a minimum toxicological risk;
2) light stability;
3) heat stability;
4) good solubility, emulsifiability or dispersibility in base substances commonly used for the preparation of cosmetic formulations;
5) negligible toxicity;
6) colour and odour which are compatible with the envisaged uses;
7) comparatively high molecular weight, therefore with a lower probability of absorption by the skin and a higher safety from the toxicological point of view;
8) compatibility with the various substances generally used in dermatological formulations.

It has surprisingly been found that the compounds of the present invention absorb very effectively UV radiations; therefore small amounts of these compounds are sufficient to obtain cosmetic formulations having a high SPF (sun protection factor).

Moreover, compounds of formula (I) have a very wide absorption, which is not localized to a very restricted area of UV spectrum. In fact, the compounds of the invention, depending on the $R_3$ and $R_4$ substituents, show absorption peaks at the same time in both the UV-B region and the UV-A region thus exerting their protecting activity from all the radiations comprised from 290 to 360 nm.

Therefore, a further object of the invention resides in the use of the compounds of formula (I) as sunscreens and light stabilisers, thanks to the capability thereof of exerting a surprising protection activity on the skin from the noxious component of sunlight radiation.

The compounds of the invention are also valuable for use in light stabilization of synthetic polymers, in order to prevent light degradations and alterations.

The compounds according to the present invention can be prepared by reacting compounds of formulae (V) and (VI)

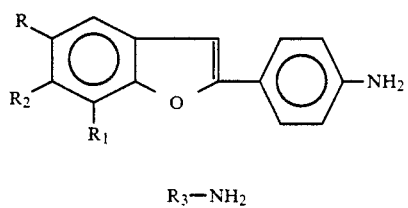
(V)

$R_3-NH_2$ (VI)

with triazine derivatives of formula (VII)

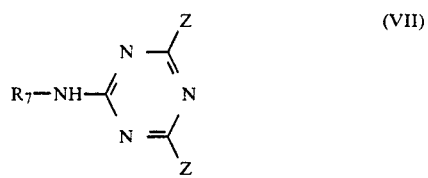
(VII)

in which Z is bromine or preferably chlorine; R, $R_1$, $R_2$ and $R_3$ have the above mentioned meanings and $R_7$ is $C_1$-$C_{18}$ alkyl, $C_5$-$C_{12}$ cycloalkyl optionally substituted with $C_1$-$C_8$ alkyl, optionally substituted aryl groups or a group of formula (II) or (III), as above defined.

The compounds of formula (V)-(VII) are known, or they can be prepared according to known methods.

Suitable solvents in which the reaction is carried out are, for example, acetonitrile; ketones, such as acetone, methyl ethyl ketones; ethers such as diethyl ether, diisopropyl ether, tetrahydrofuran, dioxane; esters such as ethyl acetate, isopropyl myristate, aliphatic or aromatic hydrocarbons such as pentane, heptane, cyclohexane, benzene, toluene, xylene or mixtures thereof.

The reaction can be effected either in the absence or in the presence of acid acceptors, such as alkali or alkaline-earth metal hydroxides, alkali metal bicarbonates or carbonates, in molar ratios of 2-3 moles of compounds of formula (V) or (VI) to mole of compounds of formula (VII).

The intermediates of formula (VII), before the subsequent reaction with the compounds of formula (V) and (VI), can be recovered and purified or, more easily, they are reacted as crude products, considering them as first step of a multi-step synthesis.

The reactions of trihalotriazines to replace the three halogen atoms with amino residues, which are the same or different, are known and widely described in technical literature, particularly in the literature concerning some kinds of dyes and optical bleachers.

According to one of the preferred embodiments of the invention, the compositions containing the compounds of formula (I) are used to protect the skin from the damaging effects of sunlight radiations.

The compounds according to the present invention can be added, of course also in combination with other stabilizers, to the cosmetic formulations as well as to synthetic polymers, generally in amounts ranging from 0.05 to 15%, preferably from 0.1 to 10% by weight of the polymer or cosmetic formulation.

The cosmetic formulations can be of various kinds and they can be used for different purposes. Generally they are in form of ointments, creams, lotions, emulsions.

The compounds of formula (I) are added either to protect the formulations themselves, for example to prevent undesired discolourations, or to protect the skin treated with the formulation from the damaging action of UV-A and UV-B radiations, which causes erythema and accelerates the ageing of the skin making it prematurely dry, wrinkled or squamous.

The following examples illustrate the invention.

EXAMPLE 1

A solution of 18.5 g of trichlorotriazine in 230 ml of acetone, cooled to 0° C., is added with 8.8 g of sodium bicarbonate, then slowly with 21 g of 4-(2benzofuranyl-)aniline keeping the temperature at 0° C. by cooling. Subsequently the mixture is stirred for ½ hour, 60 ml of water are added and stirring is continued for ½ more hour, then the formed precipitate is filtered, washed many times with water and dried under vacuum. 35 g of the dichlorotriazine derivative of formula (VIII) ($R_7$=4-(2-benzofuranyl)-phenyl) are obtained as a whitish substance with m.p. 226°-227° C.

EXAMPLES 2-4

Following the procedure of Example 1, the compounds listed in table 1 are prepared:

TABLE 1

(VIII)

$R_7$—NH—[triazine with two Cl substituents]

| Example | $R_7$ | M.P. (0° C.) |
|---|---|---|
| 2 | $C_4H_9$—CH($C_2H_5$)—$CH_2$—OOC—[phenyl]— | 245–248 |
| 3 | $(CH_3)_3C$—$CH_2$—$C(CH_3)_2$—NH—CO—[phenyl]— | 240–243 |
| 4 | $C_{14}H_{29}OOC$—[phenyl]— | 205–207 |

EXAMPLE 5

8.9 g of the compound of Example 1 and 13.2 g of 2-ethylhexyl p-aminobenzoate in 120 ml of xylene are stirred under reflux for 4 hours. Xylene is distilled off and the residue is recrystallized from a toluene and n-octane mixture. 15 g of the compound of formula (I) ($R=R_1=R_2=H$; $R_3=R_4$=4-((2-ethylhexyl)oxycarbonyl)-phenyl are obtained as a white substance with m.p. 132°–134 °C. E' is 1457 at 313 nm, 945 at 330 nm and 566 at 350 nm.

EXAMPLES 6–12

Following the procedure of Example 5, the compounds listed in table 2 are prepared:

TABLE 2

(IX)

[benzofuran-vinyl-phenyl-NH-triazine(NH-$R_3$)(NH-$R_4$)]

| Example | $R_3$ | $R_4$ | M.P. (°C.) | E' | nm |
|---|---|---|---|---|---|
| 6 | [benzofuran-CH=CH-phenyl]— | [benzofuran-CH=CH-phenyl]— | >250 | 2173<br>1909 | 335<br>351 |
| 7 | [benzofuran-CH=CH-phenyl]— | $C_4H_9$—CH($C_2H_5$)—$CH_2OOC$—[phenyl]— | 152–155 | 1614<br>1619<br>1194 | 325<br>332<br>349 |
| 8 | $C_{12}H_{25}$—NH—CO—[phenyl]— | $C_{12}H_{25}$NH—CO—[phenyl]— | 247–250 | 913<br>703<br>453 | 307<br>332<br>349 |
| 9 | [benzofuran-CH=CH-phenyl]— | $CH_3$—$C(CH_3)_2$—$CH_2$—$C(CH_3)_2$—NH—CO—[phenyl]— | 140–143 | 1490<br>1540<br>1204 | 324<br>333<br>348 |

TABLE 2-continued

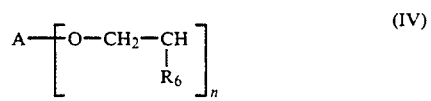

(IX)

| Example | R₃ | R₄ | M.P. (°C.) | E' | nm |
|---|---|---|---|---|---|
| 10 | (benzofuran-vinyl-phenyl group) | $C_{14}H_{29}$—OOC—(phenyl)— | 183–186 | 1428<br>1438<br>1073 | 327<br>332<br>348 |
| 11 | $CH_3$—(cyclohexyl)—OOC—(phenyl)— | $CH_3$—(cyclohexyl)—OOC—(phenyl)— | 238–241 | 1533<br>1022<br>618 | 313<br>331<br>349 |
| 12 | $C_{12}H_{25}OOC$—(phenyl)— | $C_{12}H_{25}OOC$—(phenyl)— | 167–169 | 1256<br>835<br>522 | 313<br>331<br>349 |

EXAMPLE 13

Preparation of a Sun Cream

A mixture consisting of 10 g of cyclodimeti-cone/dimeticone copolymer (Dow Corning Q 2-3223), 10 g of cyclometicone (Dow Corning 344), 0.5 g of polysorbate 20 (Tween 20) and 2 g of the compound of Example 9 is prepared.

This mixture is added to a previously prepared solution of 0.2 g of 1,1'-methylene-bis-3-(3'-hydroxymethyl-2,4-dioxy-imidazolidinyl)urea, 0.05 g of methyl paraben and 77.25 g of water.

I claim:

1. Compounds of formula (I)

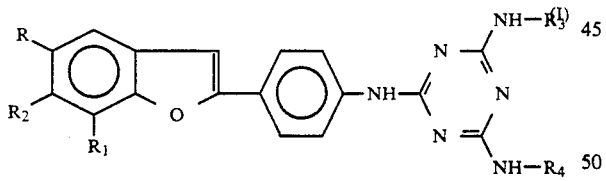

in which

R and $R_1$, which are the same or different, are hydrogen or $C_1$–$C_8$ straight or branched alkyl;

$R_2$ is hydrogen or $C_1$–$C_8$ straight or branched alkoxy;

$R_3$ and $R_4$, which are the same or different, are $C_1$–$C_{18}$ straight or branched alkyl, $C_5$–$C_{12}$ cycloalkyl optionally substituted with groups $C_1$–$C_8$ alkyl, optionally substituted aryl groups or a group of formula (II) or (III)

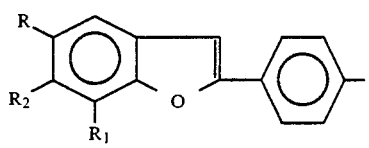

(II)

(III)

$R_5$—X—OC—(phenyl)— in which R, $R_1$ and $R_2$ have the meanings defined above, $R_5$ has the same meaning as $R_3$ and X is oxygen or the —NH— group or when X is oxygen $R_5$ can represent a group of formula (IV)

$$A \pm O-CH_2-CH \mid_{R_6} \pm_n$$  (IV)

in which A is $C_1$–$C_8$ straight or branched alkyl, $C_5$–$C_8$ cycloalkyl, optionally substituted aryl, $R_6$ is hydrogen or methyl and n can be an integer from 1 to 10.

2. Compounds according to claim 1 in which $R_3$ and $R_4$ are group of formula (II) or (III).

3. Cosmetic and dermatological compositions comprising a cosmetic or dermatological acceptable carrier and an ultraviolet light absorbing effective amount of at least one of the compounds of claim 1.

4. The compositions of claim 3 wherein said compound is contained in the composition in a sunscreen effective amount.

5. The compositions of claim 3 wherein said compound is contained in the composition in a light stabilizing amount.

6. The compositions of claim 3 wherein said compound is contained in the composition in amounts of from 0.05% to 15% by weight of the composition.

7. The compositions of claim 3 wherein the carrier is selected from the group consisting of ointments, creams, lotions and emulsions.

8. The compositions of claim 7 wherein said compound is contained in the composition in amounts of from 0.1% to 10%.

* * * * *